(12) United States Patent
Archbold et al.

(10) Patent No.: US 10,433,544 B2
(45) Date of Patent: Oct. 8, 2019

(54) HERBICIDE

(71) Applicant: University of Kentucky Research Foundation, Lexington, KY (US)

(72) Inventors: Douglas Archbold, Lexington, KY (US); Marta Nosarzewski, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/472,876

(22) Filed: Mar. 29, 2017

(65) Prior Publication Data

US 2018/0279609 A1 Oct. 4, 2018

(51) Int. Cl.
| | |
|---|---|
| *A01N 31/02* | (2006.01) |
| *A01N 25/02* | (2006.01) |
| *A01N 25/08* | (2006.01) |
| *A01N 25/12* | (2006.01) |
| *A01N 25/30* | (2006.01) |

(52) U.S. Cl.
CPC .................................. *A01N 31/02* (2013.01)

(58) Field of Classification Search
None
See application file for complete search history.

(56) References Cited

U.S. PATENT DOCUMENTS

| | | | | |
|---|---|---|---|---|
| 5,459,121 | A | * 10/1995 | Shin | A01N 31/02 426/321 |
| 6,874,277 | B2 | * 4/2005 | Yamashita | A01G 7/06 47/58.1 FV |
| 2005/0158355 | A1 | * 7/2005 | Yamashita | A01N 43/653 424/410 |

FOREIGN PATENT DOCUMENTS

| | | | |
|---|---|---|---|
| CA | 2470595 A1 | * 10/2005 | |
| WO | WO-9522253 A1 | * 8/1995 | ............. A01N 25/22 |

* cited by examiner

*Primary Examiner* — Monica A Shin
(74) *Attorney, Agent, or Firm* — Stites & Harbison PLLC; Mandy Wilson Decker; Sean P. Ritchie (57) ABSTRACT

Provided herein are SDH substrates that have use as herbicides in treating pre-emergent and post-emergent weed control. The presently-disclosed subject matter includes an herbicide including SDH substrates such as ribitol and a growth inhibitive effective amount of another adjuvant SDH substrate and/or adjuvant. Methods of treating pre-emergent and post-emergent weeds comprising applying the herbicides disclosed herein in an effective amount to suppress weed growth are also provided.

17 Claims, 8 Drawing Sheets

HERBICIDE

TECHNICAL FIELD

The presently-disclosed subject matter relates to the proposed invention is directed to compositions useful as herbicides, and their methods of use. In particular, the herbicide is a mixture of sorbitol dehydrogenase (SDH) substrates and/or inhibitors, such as natural polyols that includes ribitol, and a growth inhibitive effective amount of an adjuvant. The herbicide can be used in methods of treating pre-emergent or post-emergent weeds.

INTRODUCTION

The global herbicide market may reach $31.5 billion by 2020, with an annual growth rate of 5.4%. Synthetic herbicides dominate the global market due to abundant commercial availability, cost efficiency, and limited commercialization of bioherbicides. Glyphosate holds the largest market share. The use of bioherbicides and products of natural origin are a significant and growing interest worldwide. In addition, for both conventional and organic production systems, new modes of action are a very high priority in the weed science community, because use of but a few modes of action repeatedly on any field site can lead to the emergence of herbicide-resistant strains and the loss of effectiveness of the class, problems that have become more common. Moreover, herbicide-resistant crop technology has led to huge increases in herbicide use.

Organic horticulture relies on price premiums for economic viability, to counteract the higher costs of pest and weed control and the more labor intensive management compared to conventionally-produced crops. Organic food production is more costly than conventionally-produced food because of the regulations and limitations on the use of herbicides, pesticides, and fertilizers. The National Organic Program final rule of the USDA is that natural materials can be used in organic farming—unless they are specifically prohibited.

Organic agriculture is growing worldwide, driven by increased consumer demand, needs for resource conservation, and concerns for food security. Organic production has implications of nutritionally-improved food with fewer external inputs and reduced environmental impacts. The North American organic food and drink market was valued at $35 billion in 2013 and continued increases were predicted.

A number of organic herbicide products have appeared on the market. Organic herbicides can be effective in controlling weeds, but there are limitations. Organic herbicides kill weeds that have emerged but often have no residual activity on those emerging subsequently and established but burned-back perennial weeds can recover quickly. Since many organic herbicides kill only contacted tissue, good spray coverage is essential. Organic herbicides work if there is enough volume and concentration to make effective contact with the weeds. When herbicides and their application are expensive, hand weeding may be a cheaper alternative, especially because the organic herbicides often lack residual activity. As a result, repeat applications are necessary to control perennial weeds or new flushes of weed seedlings Thus, there is a need for compositions and methods to inhibit seed germination and kill seedlings and growing plants of many common weed species. Particularly helpful would be a potent organic herbicide that could control weeds that have grown, but also inhibit seed germination and growth of seedlings before the subsequent growth of the weeds. Such an herbicide would have utility in organic as well as in conventional production systems.

SUMMARY

The presently-disclosed subject matter meets some or all of the above-identified needs, as will become evident to those of ordinary skill in the art after a study of information provided in this document. To address the needs in the art, the presently disclosed subject matter includes herbicides effective at killing, inhibiting, suppressing or slowing growth of pre-emergent and post-emergent weeds.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

Disclosed herein are natural herbicides. The presently-disclosed subject matter includes an herbicide comprising a mixture of SDH substrates such as polyols and/or SDH inhibitors. The herbicides of the presently disclosed invention in one embodiment consist essentially of ribitol and a growth inhibitive effective amount of another SDH substrate and/or inhibitor. In some embodiments, the herbicide comprises or consists essentially of naturally occurring ribitol plus an adjuvant and optionally a surfactant. In some embodiments, the adjuvant is an SDH substrate and/or inhibitor. In some embodiments, the SDH substrate is a naturally occurring polyol. In some embodiments, the adjuvant polyol is xylitol, sorbitol, arabitol, iditol, threitol, ribitol and combinations thereof. In some embodiments, the SDH substrate and adjuvant polyl are the same.

Regarding the concentration of the natural polyols of the presently disclosed invention, the ribitol and the adjuvant are provided at a combined concentration in the range of about 40 mM to about 500 mM. In some embodiments, the ribitol and the adjuvant are provided at a combined concentration of about 2, 5, 10, 15, 20 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 550, 600, 650, 700, 750, 800, 850, 900, 950, or 1000 mM.

In some embodiments, the ribitol and the adjuvant are provided in equimolar concentrations. In other embodiments, the ribitol and the adjuvant are provided in a molar ratio of about 1:3 to 3:1 ribitol:adjuvant. In other embodiments, the ribitol and the adjuvant are provided in a molar ratio of about 1:3, 1:2, 2:1, or 3:1 ribitol:adjuvant. In some embodiments, the ribitol and the adjuvant are each provided at a concentration of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mM.

In some embodiments, the herbicide comprises ribitol and a polyol adjuvant. The herbicide can further comprise a surfactant. Additionally, the herbicide can be provided as an aqueous formulation or solid (granular, dust, gel).

Methods of treating pre-emergent and/or post-emergent weeds are also disclosed herein. In some embodiments, the method includes the step of applying an herbicide comprising or consisting essentially of a SDH substrate like ribitol and a growth inhibitive effective amount of another SDH substrate and/or inhibitor adjuvant to pre-emergent and/or post-emergent weeds.

In some embodiments, the step of applying the herbicide is performed from about 1, 2, 3, 4, 5, or 6 times a week to about 7 or more times a week. In some embodiments, the herbicide is applied at a concentration of about 150 mM ribitol and 150 mM adjuvant. In some embodiments, the herbicide is applied at a concentration of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mM ribitol, and a concentration of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mM adjuvant.

In some embodiments, the herbicide is applied to a wide variety of weeds, which can include the pre-emergent and/or post-emergent weeds.

In some embodiments, the herbicide is applied to smartweed, pigweed, lambquarters, crabgrass, purslane, hair galinsoga, morning glory, dandelion palmer amaranth, velvetleaf, foxtail, broadleaf signalgrass, cocklebur, ragweed, volunteer soybean, nutsedge, Egyptian crowfoot grass, fumitory, denticulate medick, lesser swine cress, brown beetle grass, jungle grass, tendla, false amaranth, horseweed, multiple grasses, smartweed, white clover, field bindweed, or other common weed species.

DESCRIPTION OF THE DRAWINGS

Illustrative aspects of embodiments of the present invention will be described in detail with reference to the following figures wherein:

FIG. 2 includes images of grass (A) and Dutch white clover (B) seed germination after 10 days in solutions of xylitol alone, ribitol alone, and xylitol+ribitol, at total concentrations of 100 to 300 mM (grass) or 100 to 400 mM (clover).

FIG. 3 includes images showing the effect of application of selected sugars and polyols twice a week for 2 weeks to white clover (A) and pigweed (B) plants.

FIG. 5 includes images showing exemplary control and treated plot areas in field study 1(A), where the plot was treated twice a week for three weeks; and field study 2 (B), where the plot was treated with four applications during two weeks.

FIG. 6 includes (A) a graph showing number of plants of different weed species after control application and treatment with exemplary herbicide in plots from field study 1 and (B) field study 2.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

The presently-disclosed subject matter is illustrated by specific but non-limiting examples throughout this description. The examples may include compilations of data that are representative of data gathered at various times during the course of development and experimentation related to the present invention(s). Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The presently disclosed subject matter is directed to a mixture of naturally occurring polyols, ribitol plus an adjuvant SDH substrate and/or inhibitor, such as a polyol, for use as an herbicide. The herbicide is a mixture of compounds including ribitol and substrates/inhibitors of SDH like xylitol, sorbitol or other natural or synthetic adjuvants. As used herein, the term "herbicide" or "herbicidal composition" is effective at killing, controlling, inhibiting, slowing, or otherwise adversely modifying the growth of plants. In some embodiments, for example, the herbicide of the present invention includes ribitol, and an adjuvant, for example, a natural polyol such as xylitol, sorbitol, iditol, threitol, and/or arabitol. In some embodiments, the herbicide is useful for pre-emergent and/or post-emergent growth of common weed species. The herbicide can impact seed germination and can kill seedlings and growing plants of many common weed species.

Regarding the concentration of the natural polyols of the presently disclosed invention, the ribitol and the adjuvant are provided at a combined range of about 150 mM to about 450 mM in some embodiments. In some embodiments, the combined concentration is about 300 mM. In some embodiments, the ribitol and the adjuvant are provided in equimolar concentrations. In other embodiments, the ribitol and the adjuvant are provided in a molar ratio of about 1:3 to 3:1 ribitol:adjuvant. In some embodiments, the ribitol and the adjuvant are each provided at 150 mM.

Regarding the natural SDH substrate adjuvants, such as the polyol adjuvant, the adjuvant is provided at a growth inhibitive effective amount. Such polyol adjuvant or SDH substrate is provided with ribitol and provides a higher growth inhibition together than either component alone. That is, the ribitol and adjuvant together show an enhanced or synergistic effect. The SDH substrates are, in some embodiments, selected for their ability to provide a synergistic effect with other SDH substrates such as ribitol. For example, natural SDH substrates such as polyol adjuvants can be selected from xylitol, arabitol, iditol, threitol, and sorbitol. The natural polyol adjuvant is selected for its ability to provide a synergistic effect with ribitol or another SDH substrate. The amount of polyol is also selected to provide a growth inhibitive effect. However, other natural polyol adjuvants that can be metabolized by SDH can be selected and optimized in the currently disclosed herbicide, including ribitol serving as the polyol adjuvant. In addition, the natural or synthetic SDH substrate can be metabolized by SDH. SDH inhibitors can inhibit SDH, or otherwise alter the function of SDH. Such components can be selected and optimized for use in the currently disclosed herbicide. Additionally, in some embodiments, the disclosed SDH substrate adjuvants, such as the polyol adjuvant, can be used alone for control of some weed species.

SDH substrates, as used herein, include compositions that can be metabolized by SDH. SDH inhibitors inhibit or otherwise affect, for example, decrease or reduce, the function of SDH. In particular, such SDH substrates and/or inhibitors are provided in a growth inhibitive amount in the present invention. Natural polyols such as xylitol, arabitol, iditol, threitol, and sorbitol are SDH substrates. Regarding the SDH substrate, alternative substrates with a $K_m$ similar to or lower than ribitol can include but is not limited to other polyols, deoxypolyols, and aromatic compounds (Lindstad et al., 1998). Deoxypolyols include, for example, 1,2-propanediol, 1,2-butanediol, 1,2-hexanediol, 1,6 dideoxysorbitol, 3-deoxysorbitol, 6-deoxysorbitol, as well as other hexanediols, pentadiols, butanetriols, butanediols, heptanetriols, hexantriols, decanetriols, deoxyiditols, deoxymannitols and deoxysorbitols. Aromatic substrates of SDH include (R)-1-phenyl-1,2-ethanediol, (S)-1-phenylethanol, (R)-1-phenyl-2-aminoethanol, (R)-1-(p-hydroxy)-phenyl-2-aminoethanol (octopamine), and (S)-1-O-benzylglycerol.

Inhibitors interact with SDH by coordinating the catalytic zinc ion in the substrate binding site and forming hydrophobic interactions with the cofactor NADH, sterically occluding substrate binding (Darmanin and El-Kabbani, 2001; Pauley et al., 2003). In some embodiments, the SDH inhibitor adjuvant can be a synthetically derived inhibitor of sorbitol dehydrogenase based on variations of heterocycle-substituted piperazino-pyrimidines (Chu Moyer at al. 2002; Mylari et al., 2002; Darmanin and El-Kabbani, 2001; El-Kabbani et al., 2004). The class of piperazine pyrimidines, including derivatives of 2-hydroxymethyl-4-(4-N,N-dimethylamino-sulfonyl-1-piperazino, also known as SDI 158, CP-166,572, or WAY 135,706 (Chu-Moyer et al., 2002), are effective inhibitors of SDH, often with modifications at the piperazine linker. Compounds that are designed to interact with key components of the binding site of sorbitol dehydrogenase as characterized by Pauly et al. (2003) and Darmanin and McKinley-McKee (2001, 2001), and thiol compounds (Lindstad et al., 1996) that competitively inhibit are some examples of inhibitors that can be used in the presently disclosed invention. For example, thiols may function as inhibitors due to the formation of ternary enzyme-NAD-thiol complexes, via the catalytic zinc atom (Lindstad and Mckinley-McKee (1996), facilitating NAD binding to the enzyme and vice versa. Aromatic thiols like 1-thio-1-phenylmethane and 1-thio-2-phenylethane are examples of effective SDH inhibitors.

Unmodified or natural is to be understood to denote natural compositions that have not been chemically altered or otherwise modified from their naturally occurring composition. For example, in the context of the polyols of the present disclosure, such polyols are naturally occurring and have not been modified from their natural state to include additional functional groups not found in naturally occurring polyols. Similarly, naturally occurring SDH substrates or inhibitors refers to the absence of any additional chemical functional groups on naturally occurring SDH substrates or inhibitors. Thus, unmodified or natural refers to the absence of any additional chemical functional groups on naturally occurring polyols. As used herein, "naturally derived" means that a component is obtained or derived solely from naturally occurring resources.

As used herein, the terms "effective amount" and "growth inhibitive effective amount" are used to mean a dosage sufficient to suppress growth of pre-emergent and/or post-emergent plant material. Suppressing growth of pre-emergent plant material can reduce, control, inhibit, slow, prevent, or otherwise adversely modify germination of a seed. Suppressing growth of post-emergent plant material can kill, control, inhibit, slowing, or otherwise adversely modify growth of a germinated seed or plant. Upon administration or application to plant material, including pre-emergent and post-emergent plant material, an effective amount of the herbicide over a period of time results in a constant or reduced number of plant material. The exact amount that is required will vary from plant to plant, depending on the species, maturity, and general condition of the weed, the particular carrier or adjuvant being used, mode of administration, and the like. As such, the effective amount will vary based on the particular circumstances, and an appropriate effective amount can be determined in a particular case by one of ordinary skill in the art using only routine experimentation. In some instances an effective amount is determined relative to the needs of the soil plot, weather conditions, and weed types and can be provided in a range of about 1 mM to about 1 M total concentration of ribitol and natural polyol adjuvant. In some embodiments, the total concentration of ribitol and natural polyol adjuvant is from about 200 mM to 400 mM.

The effective amount denotes an amount of the composition or of the growth inhibitor herbicides according to the present invention, which is sufficient to achieve the synergistic effects of the ribitol and adjuvant related to pre-emergent and/or post-emergent weed growth. Such an amount can vary in a broad range and is dependent on various factors, as discussed herein, such as the weed species to be controlled, the treated type of plant material, and the climatic conditions.

The period of time upon which the growth inhibitive effective amount is measured can vary dependent on several conditions such as targeted weeds, degree of infestation, weather conditions, soil conditions, crop species, mode of application, and application time. In some instances, the time period is 1, 2, 3, 4, 5, 6, 7, 8, 9, 10, 11, 12, 13, 14, 15, 16, 17, 18, 19, 20, 21, 22, 23, 24, 25, 26, 27 or 28 days. In some instance, the growth inhibitive effective amount persists for 1, 2, 3, 4, 5 or 6 weeks or more after the last application of herbicide.

The herbicide can further comprise a surfactant. Selection of surfactants is well within the skill in the art, and can be accomplished according to the herbicide formulation, for example, granular, aqueous, gel. As well known in the art, use of a surfactant would lower the total and effective amount needed for the concentrations of ribitol and the other SDH substrate adjuvant, for example, a natural polyol, or SDH inhibitor. Generally Recognized As Safe surfactants can be used, for example, vinegar (5-20% acetic acid), soaps or vegetable oils. Other surfactants can include nonionic surfactants, polysorbates such as Tween®, surfactants prepared by the reaction of octylphenol with ethylene oxide such as commercially available line of Triton X®, and nonionic organosilicone surfactants such as Silwets®.

Methods of treating pre-emergent and/or post-emergent weeds are also disclosed herein. In some embodiments, the method includes the step of applying an herbicide comprising a ribitol and a growth inhibitive effective amount of a natural polyol adjuvant to pre-emergent and/or post-emergent weeds. In some embodiments, the method includes the step of applying an herbicide comprising as active ingredient a mixture of a ribitol and a growth inhibitive effective amount of an adjuvant to pre-emergent and/or post-emergent weeds. In some embodiments, the method includes the step of applying an herbicide consisting essentially of a ribitol and a growth inhibitive effective amount of a natural polyol adjuvant to pre-emergent and/or post-emergent weeds.

In some embodiments, the step of applying the herbicide is performed from about 1 time a week to about 7 or more times a week. In some embodiments, the herbicide is applied at a concentration of about 150 mM ribitol and 150 mM adjuvant.

In some embodiments, the herbicide is applied to a wide variety of weeds, which can include the pre-emergent and/or post-emergent weeds smartweed, pigweed, lambquarters, crabgrass, purslane, hair galinsoga, morning glory, dandelion palmer amaranth, velvetleaf, foxtail, broadleaf signalgrass, cocklebur, ragweed, volunteer soybean, nutsedge, Egyptian crowfoot grass, fumitory, denticulate medick, lesser swine cress, brown beetle grass, jungle grass, tendla, false amaranth, horseweed, multiple grasses, smartweed, white clover, field bindweed, and other common weed species.

The administration or application can be continuous or intermittent. In various aspects, an herbicide can be applied or administered to treat existing plant material. In other instances an herbicide is applied prophylactically; that is, applied to prevent or treat plant material that may otherwise develop or grow.

The term "administering" or "applying" refers to any method of providing the herbicide thereof to a plant, seed, or plant material. Such methods are well known to those skilled in the art and include, but are not limited to, spraying, spreading, and other applications based on formulation type of herbicide.

The amount of herbicide employed is sufficient to suppress the growth of plant material. The minimum amount of herbicide employed is the amount at which growth suppression becomes observable by visual inspection or other means known in the art.

Application of the herbicide to the plant material for weed control can vary in time applied. In some embodiments, the herbicide is applied to the plant material 1, 2, 3, 4, 5, 6 or 7 or more times a week. In some embodiments, the herbicide is applied one to three times a week.

Examples of herbicide compositions are solutions, emulsions, suspensions, dusts, powders, pastes and granules. The composition type depends on the particular intended purpose; in each case, it should ensure a fine and uniform distribution of the compound according to the invention. More precise examples for composition types are suspensions, pastes, pastilles, wettable powders, dusts or granules which can be water-soluble or wettable, as well as gel formulations. Usually composition types such as suspensions and gel formulations are employed diluted. Composition types such as granules, wettable powders and dusts are typically used undiluted. In one embodiment, the herbicide is provided as an aqueous or solid formulation.

The term "plant material" is to be understood to denote all parts of the plant such as seeds, seedlings, vegetative plant material such as cuttings, tubers, seeds, roots, fruits, tubers, bulbs, rhizomes, shoots, sprouts and other parts of plants, including leaves, young and mature plants. The term "plant material" is to be understood to include both pre-emergent and post-emergent material.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an enzyme" includes a plurality of such enzymes, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Those of ordinary skill in the art will recognize factors and methods for application and/or treatment of weed species plant material. Factors that can contribute to the variations in application of the herbicide include, but are not limited to, weed species, maturity of the plant material and whether said plant material is pre-emergent or post-emergent, climate conditions including rainfall and humidity, soil conditions including soil content, as well as other factors for herbicide use.

EXAMPLES

The presently-disclosed subject matter is further illustrated by the following specific but non-limiting examples. The examples may include compilations of data that are representative of data gathered at various times during the course of development and experimentation related to the presently-disclosed subject matter. Furthermore, some of the examples described herein may be prophetic examples.

Prior work (Nosarzewski et al., 2012) showed that *Arabidopsis thaliana* knockout mutant plants lacking functional sorbitol dehydrogenase (SDH) activity accumulated 10-14-fold more ribitol than wild-type (WT) plants and died even though re-watered. SDH is the primary enzyme responsible for metabolizing ribitol to ribulose and sorbitol to fructose in *Arabidopsis*. SDH also converts xylitol to xylulose. The sdh mutant plants accumulated ribitol to abnormally high levels due to lack of ribitol metabolism. It was believed that the abnormally high ribitol content was toxic, which was demonstrated by application of 50 mM ribitol to well-watered sdh-knockout mutant plants. The toxicity of an abnormally high ribitol content was demonstrated by application of 50 mM ribitol to well-watered sdh-knockout mutant plants. Such application resulted in their quick injury and eventual death, but had no effect on Wild Type plants. It was also previously shown that ribitol inhibited seed germination when it cannot be metabolized properly, but no other polyols metabolized by SDH were effective (Nosarzewski et al., 2012).

However, our subsequent work with numerous plant species indicated that the ribitol toxicity effect on seed germination occurred at concentrations equal to or greater than 300 mM ribitol with no adjuvant, or at lower ribitol concentrations with an adjuvant. An increasing number of species have been identified as bearing the SDH gene and activity (Jia et al., 2105), so most weed species could likely metabolize it.

SDH metabolizes sorbitol, xylitol, iditol, threitol and rabitol. Thus the presently disclosed subject matter utilizes another polyol along with ribitol in the application to a seed or plant. Without being bound by theory it is believed the other polyol, xylitol, sorbitol, arabitol, etc., will be a competitor for SDH and reduce the rate of ribitol metabolism, leaving the ribitol content high enough to cause injury, suppression and/or death to the plant material which includes but is not limited to inhibition of seed germination, killing seedlings, and as a post-emergent suppression and/or killing of growing plants. Thus, the following experiments were conducted to develop and evaluate an herbicide of natural products.

Example 1: Seeds

It was believed that the toxic effect of ribitol accumulation in the plant tissue can be obtained by saturating the tissue with ribitol solution alone or by a mixture consisting of ribitol and another SDH substrate or substrates, either of which will sustain a high concentration of ribitol that is toxic. Sorbitol and xylitol are SDH substrates (Lindstad et al., 1998) and they were included in a formulation with ribitol. Both sorbitol and xylitol are present in plants like ribitol at very low levels, are natural products, are inexpensive compared to ribitol, and are considered as generally recognized as safe substances (GRAS) by the U.S. Food and Drug Administration.

Figure 1:
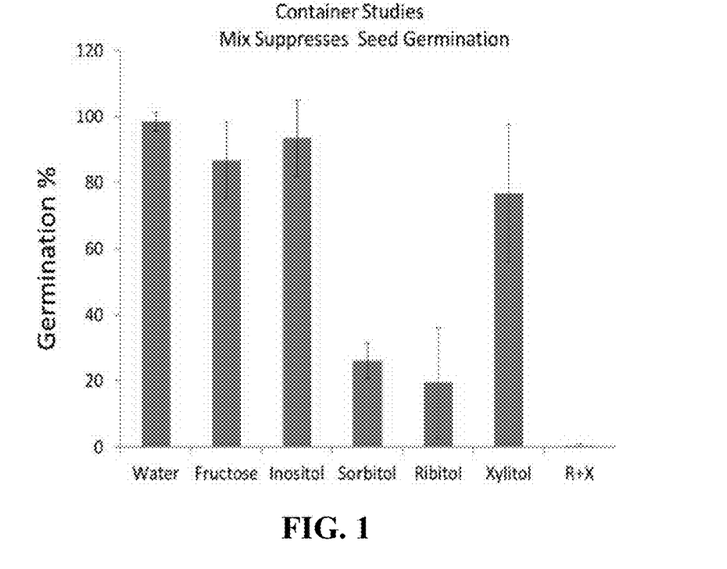
FIG. 1 includes a chart showing the effect of 300 mM solutions of fructose and polyols, and a 150 mM ribitol plus 150 mM xylitol (R+X) formulation on seed germination. Means±standard deviation are across alfalfa, dandelion and mixed grasses after 8 days of incubation.

Seed of several species were incubated with 300 mM solutions of fructose, inositol, sorbitol, ribitol, xylitol as well as a ribitol/xylitol solution. As shown in FIG. 1, the seeds were only significantly inhibited by the ribitol/xylitol solution, with a synergistic effect exhibited by application of the combination of ribitol and an additional polyol.

Figure 2A:
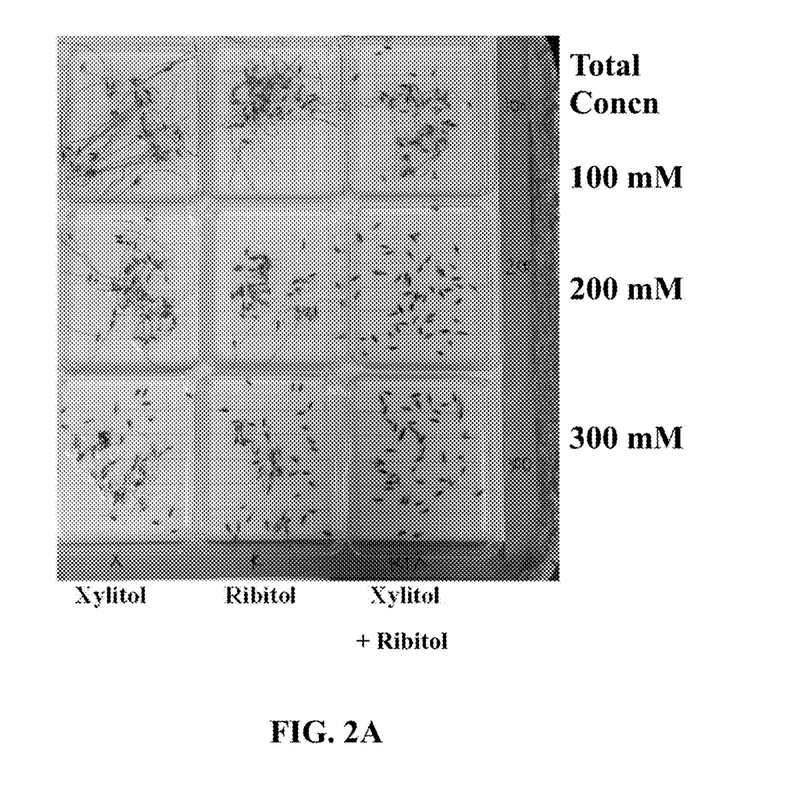
Figure 2B:
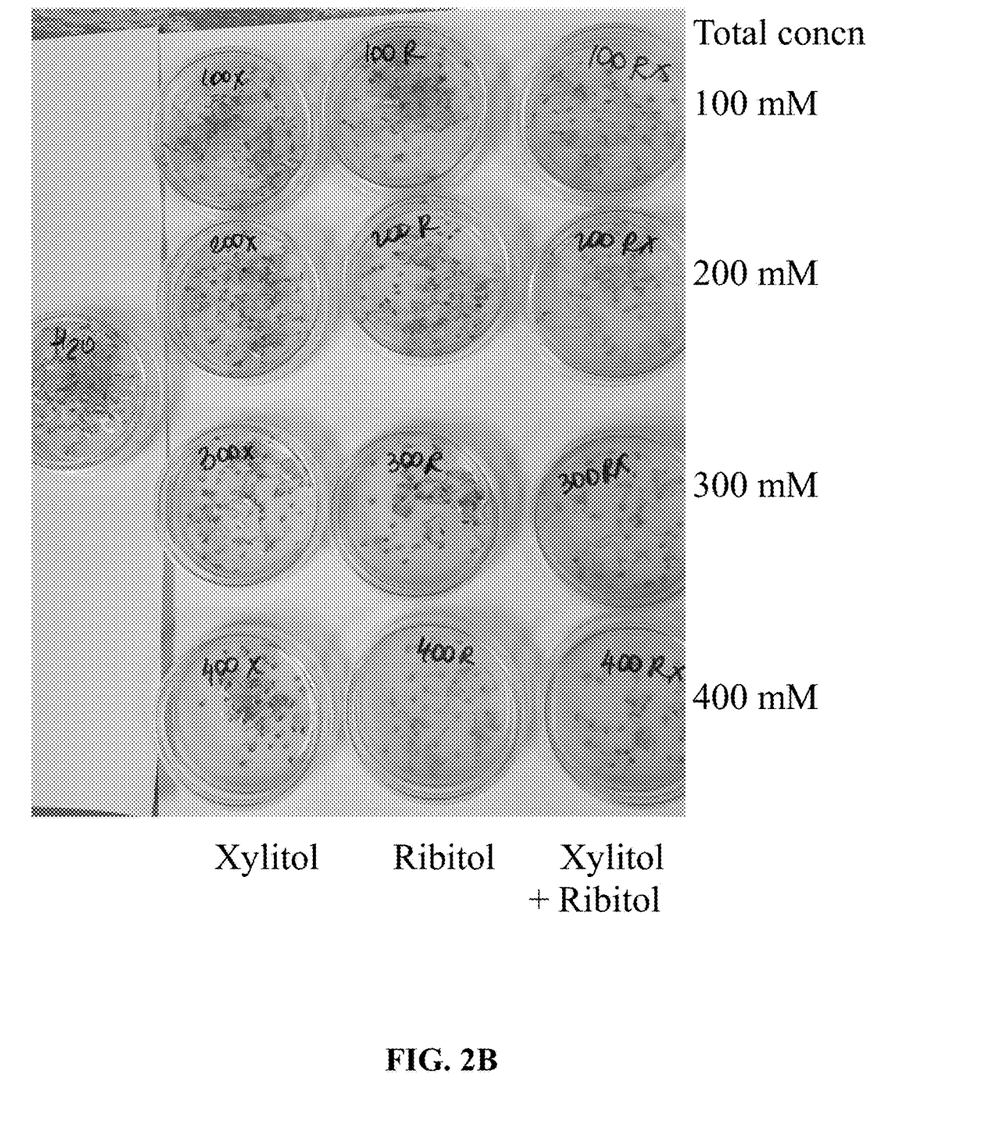

Seed of turfgrass (FIG. 2A) and Dutch white clover (FIG. 2B) were incubated with solutions of xylitol, ribitol, and a ribitol/xylitol solution at 100 to 300 mM (A) or 100 to 400 mM (B). The grass seed was significantly inhibited by ribitol alone at 300 mM, and by ribitol/xylitol at 200 mM. The clover seed was in developmental arrest at 400 mM ribitol and 300 mM ribitol/xylitol. Both grass and clover seedlings transferred from polyol solution to water also failed to resume germination or growth (data not shown).

Example 2: Container Studies

Figure 3A:
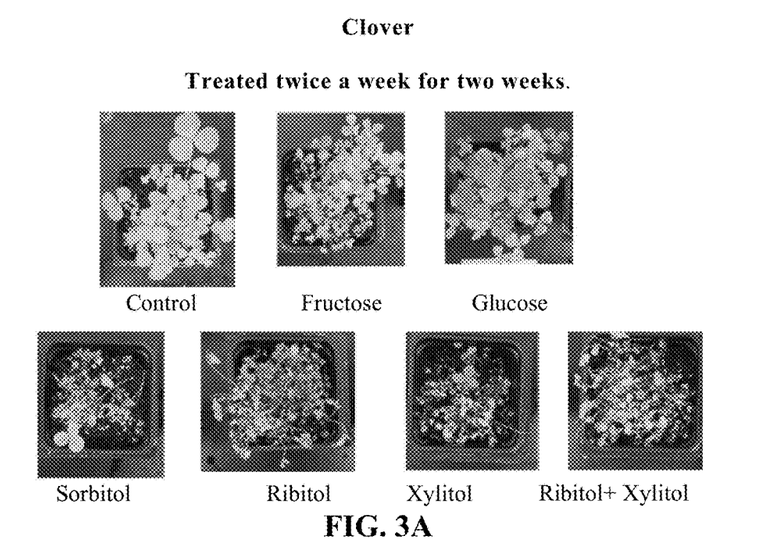
Figure 3B:
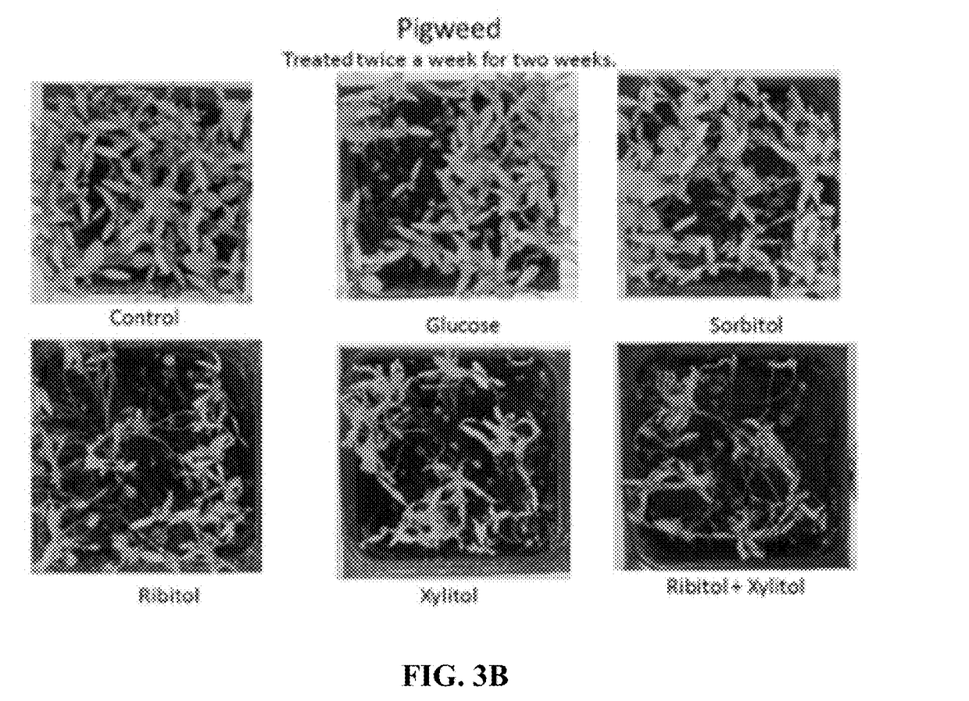
Figure 4:
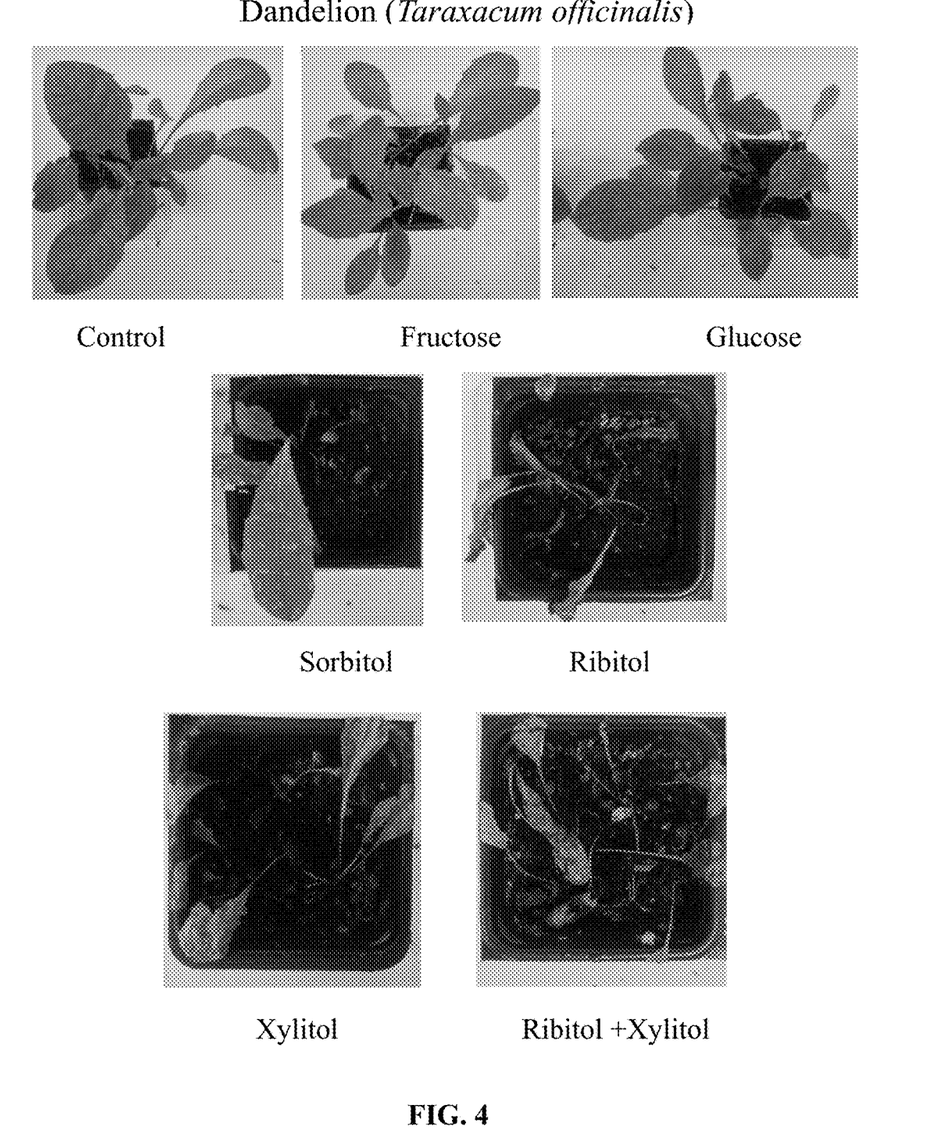
FIG. 4 includes images showing the effect of application of 300 mm fructose, glucose, sorbitol, ribitol, xylitol, or ribitol+xylitol (each at 150 mM) twice weekly for 2 weeks on dandelion plants.

In container studies, fructose, inositol, sorbitol, ribitol, xylitol as well as a ribitol/xylitol solution were applied at 300 mM total concentration to plants including white clover and pigweed. The ribitol, xylitol, and sorbitol application to growing plants of several weed species, including clover and pigweed, caused injury and death, with the effect of sorbitol<xylitol≤ribitol (FIG. 3). Other common sugars like glucose and fructose had no effect. Similarly, dandelion plants were sprayed with 300 mm fructose, glucose, sorbitol, ribitol, xylitol, or ribitol+xylitol (each at 150 mM) twice weekly for 2 weeks with death of plants from ribitol, xylitol, and their combination (FIG. 4). Although sorbitol and xylitol also caused damage, the 300 mM ribitol/xylitol formulation had the most severe effect across the greatest number of species. Due to the desire for a broad spectrum herbicide that affected both seed germination and plant growth the most, and to keep the most expensive component, ribitol, to a low effective level, we concluded that the 150 mM ribitol/150 mM xylitol formulation (300 mM combined concentration) was the optimum for field tests.

Example 3: Field Trials

Figure 5A:
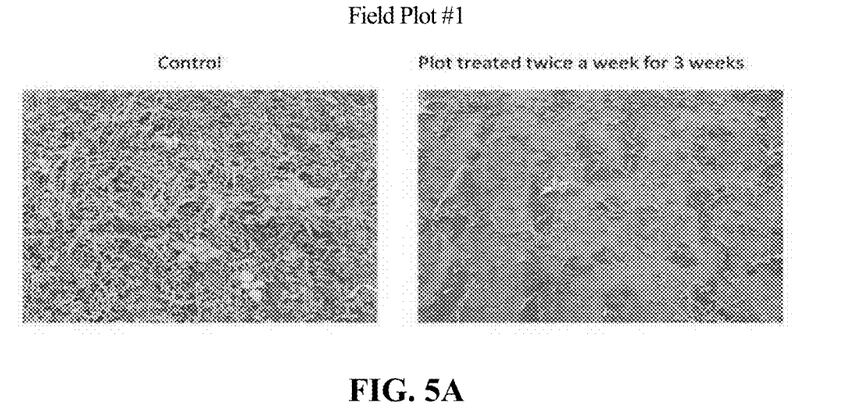
Figure 5B:
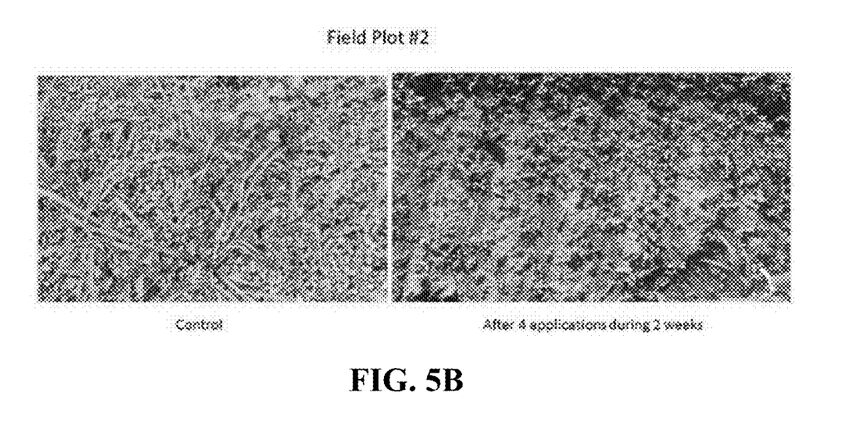
Figure 6A:
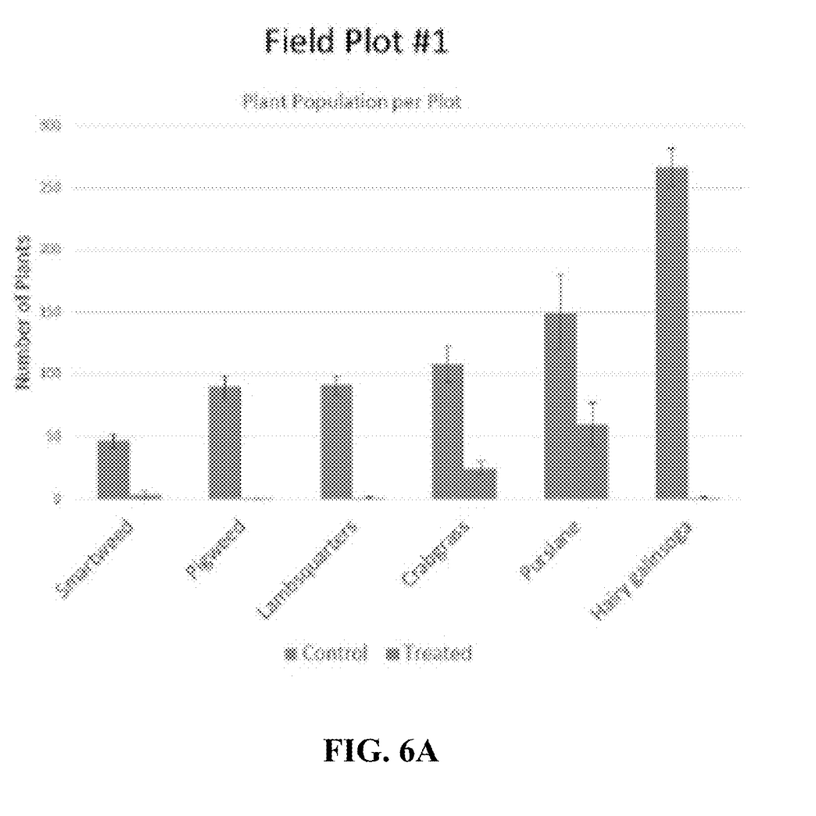
Figure 6B:
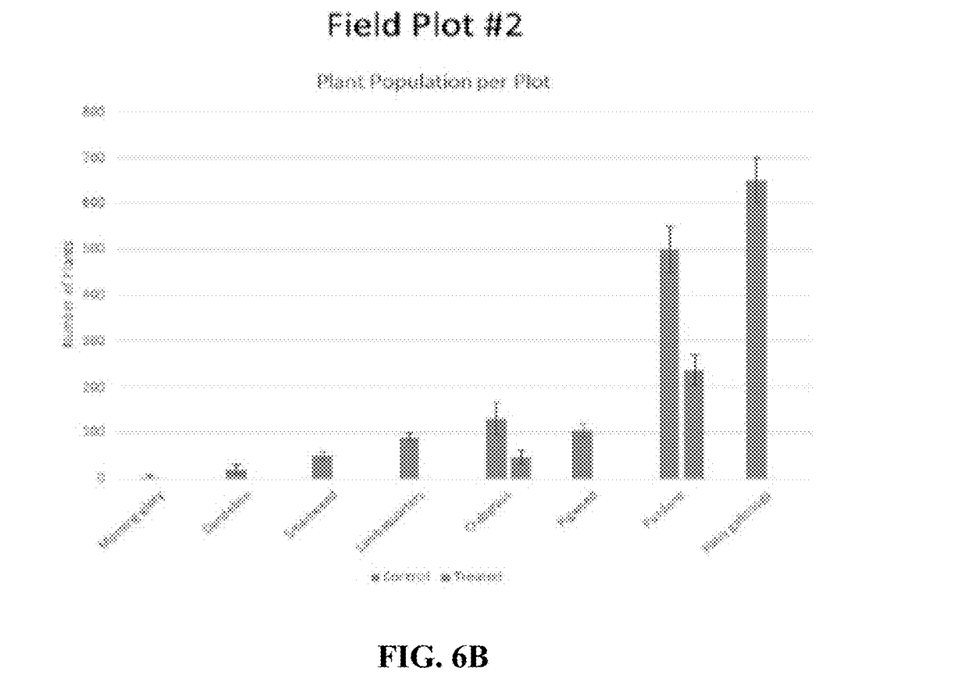

In field trials in May-July at the Horticulture Research Farm in Lexington, two separate field plots with differing weed populations were used. Applications of the ribitol/xylitol formulation (each at 150 mM) were applied twice a week for 4 weeks to replicated 1 m² subplots. Results were recorded 4-6 weeks after the last application. Emerging weed populations were reduced 10- to 50-fold, although a few species such as purslane were suppressed but not as reduced in number (FIGS. 5, 6). As shown in FIGS. 5A and 5B, images of the plots show significant suppression after a plot was treated with herbicide twice a week for three weeks (FIG. 5A) and after four applications over two weeks (FIG. 5B) according to the current experiment.

Figure 7:
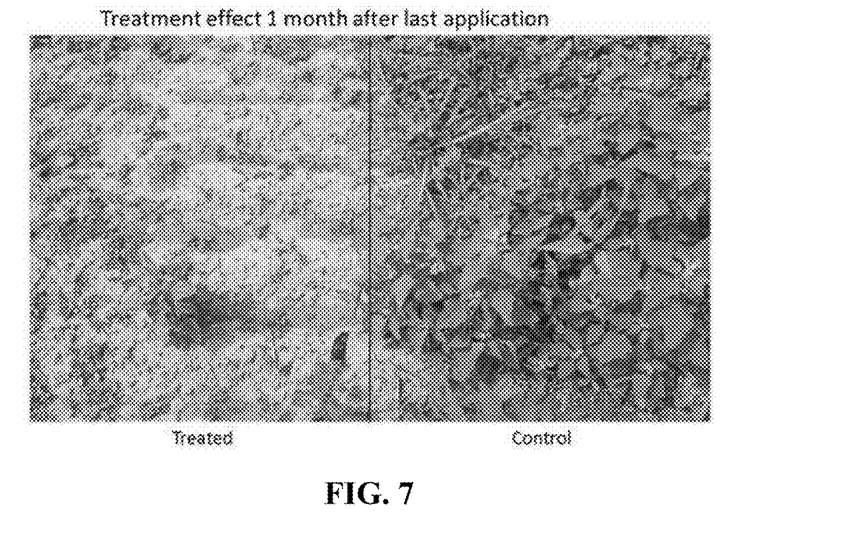
FIG. 7 includes images showing the lasting treatment effect on plots one month after last exemplary herbicide and control application.

The herbicidal effect of the ribitol/xylitol formulation persisted in the month after the final applications, as weed emergence was slow and low in number (FIGS. 6, 7). As shown in FIG. 6, even a month after the final applications, smartweed, pigweed, lambquarters, crabgrass, purslane, hair galinsoga, morning glory and dandelion remained significantly inhibited or reduced on the plots treated with an exemplary herbicide. Rainfall from May through July on the site was considered average to above average, so it was clear that the herbicidal effect was not lost or 'washed away', a highly desirable trait for any herbicide.

Example 4: Ribitol and SDH Specific Inhibitor

Figure 8:
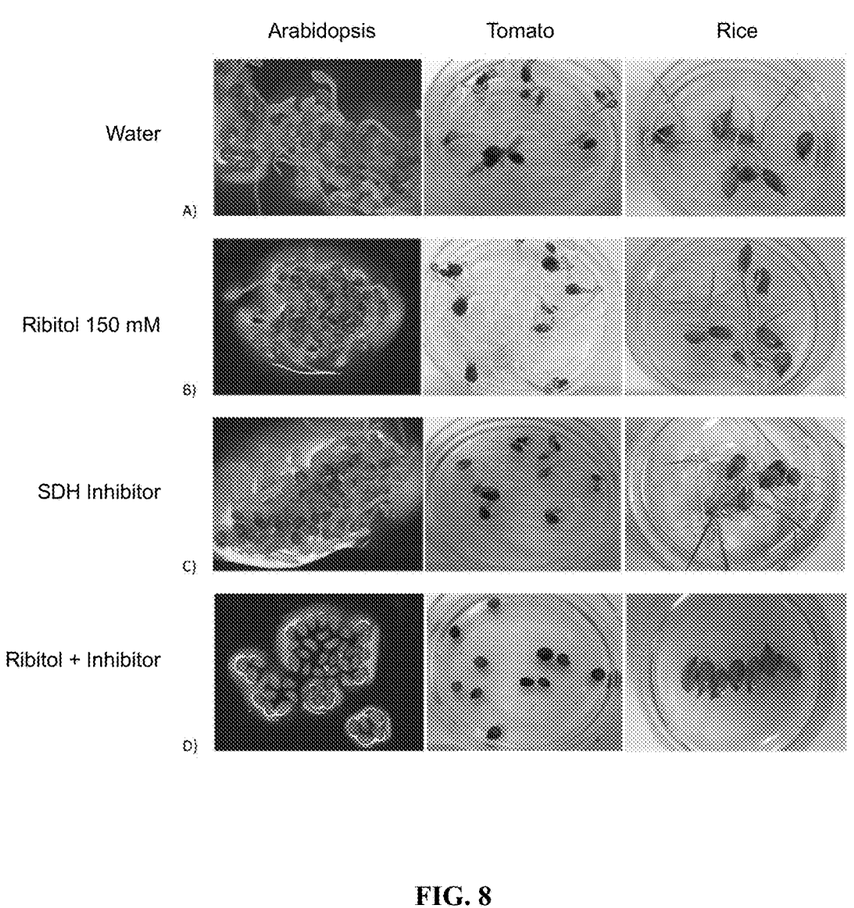
FIG. 8 includes images showing the effect of blocking SDH activity with (A) water (B) 150 mM ribitol (C) the SDH-specific inhibitor CP-470711(Pfizer) and (D) ribitol+CP-470711 on sensitivity of seed germination of Wild Type *Arabidopsis*, tomato, and rice for 6 days.

The effect of blocking SDH activity with an SDH specific inhibitor was explored with application to wild type *Arabidopsis*, tomato and rice seeds for six days. As shown in FIG. 8, only application of 150 mM ribitol with the SDH specific inhibitor CP-470711 (Pfizer) at 0.5 mM together showed effective inhibition of seed germination in *Arabidopsis*, tomato and rice seeds (FIG. 8D). Each compound alone at the same concentration had no effect.

Discussion

The ribitol/xylitol formulation functioned within both major classes of herbicides, as a pre-emergent type that inhibits seed germination and kills seedlings, and as a post-emergent type that suppress and/or kills growing plants. Features of one effective formulation include an herbicidal effect created when plants are treated with a mixture of a natural but herbicidal compound (ribitol) and another adjuvant compound (xylitol and/or sorbitol) that is metabolized by the same enzyme as ribitol, thus reducing the rate of ribitol metabolism and sustaining a high ribitol concentration that is toxic. Additionally, this proposed herbicide could also be formulated strictly for the conventional agricultural market by replacing either natural polyols with synthetic polyol analogs and/or other synthetic SDH substrates or inhibitors.

The herbicide appears to provide a new mode of action to the herbicide industry, never before exploited for herbicide use. Moreover, all compounds in the formulation are naturally-derived, with potential in organic production systems, the most rapidly growing sector of crop agriculture, as well as in conventional systems.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a protein" includes a plurality of such proteins, and so forth.

As used herein, "optional" or "optionally" means that the subsequently described event or circumstance does or does not occur and that the description includes instances where said event or circumstance occurs and instances where it does not. For example, a composition including a first component, a second component, and optionally a third component means that the composition includes the first and second components, or it includes the first, second, and third components.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the present disclosure can be changed without departing from the scope of the subject matter disclosed herein. Furthermore, the foregoing description is for the purpose of illustration only, and not for the purpose of limitation.

Throughout this document, various references are mentioned. All such references are incorporated herein by reference, including the references set forth in the following list:

Allied Market Research, Allied Analytics LLP, Portland, Oreg. 2014. World Herbicides Market—Opportunities and Forecasts, 2013-2020 Forecast. 130 pp.

Duke, S. O. 2012. Why have no new herbicide modes of action appeared in recent years? Pest Management Science. 68: 505-512.

Jia, Y., D. C. J. Wong, C. Sweetman, J. B. Bruning, and C. M. Ford. 2105. New insights into the evolutionary history of plant sorbitol dehydrogenase. BMC Plant Biology 15:101.

Lindstad, R. I., P. Köll, and J. S. McKinley-McKee. 1998. Substrate specificity of sheep liver sorbitol dehydrogenase. Biochemical Journal 15: 479-487.

Nosarzewski, M., A. B. Downie, B. Wu, and D. D. Archbold. 2012. The role of SORBITOL DEHYDROGENASE in *Arabidopsis thaliana*. Functional Plant Biology 39: 462-470.

Banavara L. Mylari,* Peter J. Oates, William J. Zembrowski, David A. Beebe, Edward L. Conn, James B. Coutcher, Melissa T. O'Gorman, Michael C. Linhares, and Gregory J. Withbroe. 2002. A Sorbitol Dehydrogenase Inhibitor of Exceptional in Vivo Potency with a Long Duration of Action: 1-(R)-{4-[4-(4,6-Dimethyl[1,3,5]triazin-2-yl)-2R,6S-dimethylpiperazin-1-yl]pyrimidin-2-yl}ethanol. J. Medicinal Chemistry. 45:4398-4401.

Chu-Moyer, M. Y., W. E. Ballinger, D. A. Beebe, R. Berger, J. B. Coutcher, W. W. Day, J. Li, B. L. Mylari, P. J. Oates, and R. M. Weekly. 2002. Orally-Effective, Long-Acting Sorbitol Dehydrogenase Inhibitors: Synthesis, Structure—Activity Relationships, and in Vivo Evaluations of Novel Heterocycle-Substituted Piperazino-Pyrimidines. J. Medicinal Chemistry. 45:511-528.

Darmanin, C. and O. El-Kabbani. 2000. Modelling studies on the binding of substrate and inhibitor to the active site of human sorbitol dehydrogenase. Bioorganic & Medicinal Chemistry Letters. 10: 1101-1104.

Darmanin, C. and O. El-Kabbani. 2002. Modelling studies of the active site of human sorbitol dehydrogenase: an approach to structure-based inhibitor design of the enzyme. 11: 3133-3136.

El-Kabbani, O.; Darmanin, C.; Chung, R. P.-T. 2004. Sorbitol Dehydrogenase: Structure, Function and Ligand Design. Curr. Medicinal Chemistry 11: 465-476.

Lindstad, R. I., and J. S. McKinley-McKee. 1996. Reversible Inhibition of Sheep Liver Sorbitol Dehydrogenase by Thiol Compounds. Eur. J. Biochem. 241: 142-148.

Pauly, T. A., J. L. Ekstrom, D. A. Beebe, B. Chrunyk, D. Cunningham, M. Griffor, A. Kamath, S. E. Lee, R. Madura, D. Mcguire, T. Subashi, D. Wasilko, P. Watts, B. L. Mylari, P. J. Oates, P. D. Adams, V. L. Rat. 2003. X-Ray Crystallographic and Kinetic Studies of Human Sorbitol Dehydrogenase. Structure 11:1071-1085.

What is claimed is:

1. An herbicide, comprising active ingredients consisting of: ribitol; and a growth inhibitive effective amount of an SDH substrate and/or inhibitor adjuvant.

2. The herbicide of claim 1, wherein the adjuvant is selected from the group consisting of polyols, deoxypolyols, aromatic compounds and combinations thereof.

3. The herbicide of claim 1 wherein the adjuvant is a natural polyol.

4. The herbicide of claim 1, wherein the adjuvant is selected from the group consisting of xylitol, sorbitol, arabitol, iditol, threitol and mixtures thereof.

5. The herbicide of claim 2, wherein the adjuvant is selected from the group consisting of xylitol, sorbitol, iditol, β-sedoheptitol, 1,2-hexanediol, 3-deoxysorbitol, 6-deoxysorbitol, (R)-1-phenyl-1,2-ethanediol, and combinations thereof.

6. The herbicide of claim 1, wherein the adjuvant is an SDH inhibitor.

7. The herbicide of claim 6, wherein the SDH inhibitor is selected from the group consisting of a piperazine pyrimidine, 1-thio-1-phenylmethane and 1-thio-2-phenylethane.

8. The herbicide of claim 1, wherein the ribitol and the adjuvant are provided at a combined concentration of from about 150 mM to about 450 mM.

9. The herbicide of claim 1, wherein the ribitol and the adjuvant are each provided at a concentration of about 150 mM to 200 mM.

10. The herbicide of claim 1, wherein the ribitol and the adjuvant are provided at a ratio of between about 1:3 to 3:1 ribitol:adjuvant.

11. The herbicide of claim 1, wherein the herbicide is an aqueous or solid formulation.

12. The herbicide of claim 1, further comprising a surfactant.

13. The herbicide of claim 12, wherein the surfactant is selected from the group consisting of vinegar, soap, vegetable oil, and a nonionic detergent.

14. A method of treating pre-emergent and/or post-emergent weeds, comprising: applying the herbicide of claim 1 to pre-emergent and/or post-emergent weeds.

15. The method of claim 14, wherein the applying is performed from about 1 time a week to about 7 times a week.

16. The method of claim 14, wherein the herbicide is applied at a concentration of about 150 mM ribitol and 150 mM adjuvant.

17. The method of claim 14, wherein the pre-emergent and/or post-emergent weed is selected from the group consisting of smartweed, pigweed, lambquarters, crabgrass, purslane, hair galinsoga, morning glory, dandelion palmer amaranth, velvetleaf, foxtail, broadleaf signalgrass, cocklebur, ragweed, volunteer soybean, nutsedge, Egyptian crowfoot grass, fumitory, denticulate medick, lesser swine cress, brown beetle grass, jungle grass, tendla, false amaranth, horseweed, multiple grasses, smartweed, white clover, field bindweed, grasses, other common weed species, and combinations thereof.

* * * * *